United States Patent [19]

Lombardino

[11] 4,307,106

[45] Dec. 22, 1981

[54] AMINOTHIAZOLES

[75] Inventor: Joseph G. Lombardino, Niantic, Conn.

[73] Assignee: Pfizer Inc., New York, N.Y.

[21] Appl. No.: 94,785

[22] Filed: Nov. 16, 1979

Related U.S. Application Data

[63] Continuation-in-part of Ser. No. 911,830, Jun. 2, 1978, abandoned.

[51] Int. Cl.$^3$ .......................................... C07D 277/38
[52] U.S. Cl. .................................. 424/270; 548/190; 548/193
[58] Field of Search ................. 548/190, 193; 424/270

[56] References Cited

U.S. PATENT DOCUMENTS 3,299,087  1/1967  Spivack et al. ...................... 548/190
3,458,526  7/1969  Lednicer ............................ 548/193

FOREIGN PATENT DOCUMENTS 1192350  5/1965  Fed. Rep. of Germany .
1188846  4/1970  United Kingdom .

OTHER PUBLICATIONS

Kaye et al., JACS 74, 2271 (1952).
Bhattacharya, Jour. Ind. Chem. Soc. 44, 57 (1967).
Biniecki et al., Acta Polon. Pharm. 19, 103 (1962).
CA 59, 1613e (1963).

*Primary Examiner*—Nicholas S. Rizzo
*Attorney, Agent, or Firm*—Connolly and Hutz

[57] ABSTRACT

A series of 2-aralkylaminothiazoles and the pharmaceutically acceptable acid addition salts thereof having anti-inflammatory and immune regulant activity are disclosed. Preferred compounds include 2-phenethylamino-4-phenyl-thiazole, 2-(p-methoxyphenethylamino)-4-(p-fluorophenyl)-thiazole, 2-phenethylamino-4-phenyl-5-methyl-thiazole, 2-thenylamino-4-phenyl-thiazole and 2-thenylamino-4-(p-fluorophenyl)-thiazole.

34 Claims, No Drawings

AMINOTHIAZOLES

BACKGROUND OF THE INVENTION

This application is a continuation-in-part of application Ser. No. 911,830 filed June 2, 1978 and now abandoned.

This invention relates to novel substituted aminothiazoles useful for relieving inflammatory conditions and as immune regulants.

A number of compounds have been known in the art to be useful as anti-inflammatory agents, for example the cortico steroids, phenylbutazone, indomethacin and various 3,4-dihydro-4-oxo-2H-1,2-benzothiazine-4-carboxamide-1,1-dioxides, such as those disclosed in U.S. Pat. No. 3,591,584. Accordingly, these compounds have been of therapeutic value in the treatment of arthritic and other inflammatory conditions such as rheumatoid arthritis. Such conditions have also been treated by administration of immunoregulatory agents, such as levamisole, as described for example in Arthritis Rheumatism, 20, 1445 (1977) and Lancet, 1, 393 (1976). In efforts to find new and improved therapeutic agents for the treatment of these conditions, it has now been found that the novel aminothiazoles of the present invention have a particularly desirable combination of pharmacological properties, namely that they are active both as anti-inflammatory agents and as regulants of the immune response in the body. Accordingly, they are of particular value in the treatment of rheumatoid arthritis and other conditions where relief of the inflammation and regulation of the body immune response is desired.

The synthesis of a limited number of 2-aralkylaminothiazoles has been described in the art, for example 2-phenethylaminothiazole, Chem. Abs. 59, 1613e (1963); 2-benzylaminothiazole. J.A.C.S., 74, 2272 (1952) and 2-benzylamino-4-phenyl-thiazole, J. Ind. Chem. Soc., 44, 57 (1967). These articles do not, however, disclose any pharmacological activity of such compounds. 2-Benzylamino-4,5-bis(p-methoxyphenyl)-thiazole and substituted-benzylamino analogs thereof having anti-inflammatory activity are described in U.S. Pat. No. 3,458,526.

SUMMARY OF THE INVENTION

This invention relates to substituted animothiazoles useful as anti-inflammatory agents and as regulants of the body immune response. More particularly, the novel compounds of this invention are those of the formula

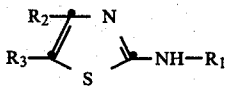

and the pharmaceutically acceptable acid addition salts thereof, wherein $R_1$ is selected from $-(CH_2)_2-X$, and $-(CH_2)_mY$, wherein X is selected from phenyl and monosubstituted phenyl, said substituent being selected from alkyl of 1 to 3 carbon atoms, hydroxy, alkoxy of 1 to 3 carbon atoms, chloro, bromo and fluoro; Y is selected from thienyl, monosubstituted thienyl, furyl and monosubstituted furyl, said substituent being selected from alkyl of 1 to 3 carbon atoms, chloro, bromo and fluoro; m is an integer from 1 to 2; $R_2$ is selected from phenyl, thienyl and monosubstituted phenyl, said substituent being selected from alkyl of 1 to 3 carbon atoms, chloro, bromo and fluoro; and $R_3$ is selected from hydrogen and alkyl of 1 to 3 carbon atoms. Preferred substituents for $R_2$ are phenyl and p-fluorophenyl and for $R_3$ are hydrogen and methyl.

A preferred group of compounds is that wherein $R_1$ is $-(CH_2)_2-X$. Most preferred are those compounds where X is phenyl or p-methoxyphenyl, $R_2$ is phenyl or p-fluorophenyl and $R_3$ is hydrogen or methyl, including 2-phenethylamino-4-phenyl-thiazole, 2-(p-methoxyphenylamino)-4-(p-fluorophenyl)-thiazole and 2-phenethylamino-4-phenyl-5-methyl-thiazole.

A further group of interest is that wherein $R_1$ is $-(CH_2)_m-Y$, especially where $R_2$ is phenyl or p-fluorophenyl and $R_3$ is hydrogen or methyl, especially where m is 1. Preferred groups for Y are thienyl and furyl, including 2-thenylamino-4-phenyl-thiazole, 2-thenylamino-4-(p-fluorophenyl)-thiazole, 2-furfurylamino-4-phenyl-thiazole and 2-furfurylamino-4-phenyl-5-methyl-thiazole.

Also embraced by the present invention are pharmaceutical compositions comprising a novel substituted aminothiazole of this invention, as described above herein, or a pharmaceutically acceptable acid addition salt thereof, together with a pharmaceutically acceptable carrier or diluent. Preferred pharmaceutical compositions are those containing the preferred compounds described above and most preferably containing 2-phenethylamino-4-phenyl-thiazole, 2-thenylamino-4-(p-fluorophenyl)-thiazole or 2-(p-methoxy-phenethylamino)-4-(p-fluorophenyl)-thiazole or pharmaceutically acceptable acid addition salts of these compounds.

Also claimed is a method of treating rheumatoid arthritis in a host which comprises administering to said host an effective anti-arthritic amount of a novel aminothiazole of this invention, especially those preferred compounds described above and most preferably 2-phenethylamino-4-phenyl-thiazole, 2-(p-methoxyphenethylamino)-4-(p-fluorophenyl)-thiazole or 2-thenylamino-4-(p-fluorophenyl)-thiazole or pharmaceutically acceptable acid addition salts thereof.

DETAILED DESCRIPTION OF THE INVENTION

The novel aminothiazoles of this invention are prepared from an appropriately substituted N-aralkylthiourea of the formula

where $R_1$ is as previously defined. The latter compounds are readily prepared from known and readily available amines of the formula $R_1NH_2$. For example, when the group $R_1$ is $-(CH_2)_2-X$, unsubstituted or appropriately substituted phenethylamines are employed. Analogous thienyl or furyl amines will be used to prepare compounds where $R_1$ is $-(CH_2)_m-Y$. In the above, X, Y, and m are as previously defined. The amine starting material is first converted to the hydrochloride or other hydrohalide salt by reaction with hydrogen chloride or other hydrogen halide, generally by bubbling the gas into a solution of the amine in an inert organic solvent, typically an ether such as diethyl ether, at a temperature of about $-10°$ C. to about $10°$ C. The amine hydrohalide salt is then reacted with ammonium thiocyanate or an alkali metal thiocyanate, such as potassium thiocyanate, in an inert organic solvent, generally an aromatic solvent such as bromobenene, chlorobenzene, xylene and the like, to form the desired N-aralkylthiourea. The reaction is preferably conducted in an inert atmosphere, for example under nitrogen, at a temperature of about 110° C. to about 250° C., preferably 150° C. to 200° C., for example at the reflux temperature in bromobenzene. The reaction will generally be complete in about 30 minutes to about 6 hours depending on the temperature employed, generally in about 1 to 3 hours at 150° to 200° C. In preparing the N-aralkylthioureas as described above, it is usually found that some bis-aralkyl substituted thiourea is formed, but this can be readily separated from the desired monosubstituted product, for example by recrystallization.

The appropriate N-aralkylthiourea is converted to the desired aminothiazole by reaction with an appropriately substituted α-halo ketone or aldehyde of the formula $R_2COCH(Z)R_3$, wherein $R_2$ and $R_3$ are as previously defined and Z is halo, preferably chloro or bromo. For example, when $R_2$ is phenyl and $R_3$ is hydrogen, α-bromoacetophenone may be employed. Other appropriate α-halo ketones or aldehydes will be readily selected in order to give the desired $R_2$ and $R_3$ substituents in the thiazole ring. The reaction is conducted in an inert organic solvent, typically an n-alkanol of 1 to 6 carbon atoms, preferably in absolute ethanol. Reaction temperatures between about 50° and 175° C. are employed, preferably the reflux temperature of the solvent. The reaction is preferably conducted in an inert atmosphere, for example, under nitrogen or another inert gas. The reaction is generally essentially complete in about 1 to 15 hours depending on the temperature employed, for example in about 1 to 4 hours when using ethanol at reflux temperature. The desired compound will be obtained as the hydrohalide salt and the free base can then be prepared from the salt by conventional means, for example by contacting with an excess of a base such as an alkali metal hydroxide or carbonate, followed by extraction of the desired free base aminothiazole with a suitable organic solvent, for example an ether like diethyl ether.

The pharmaceutically acceptable acid addition salts of the novel aminothiazoles are also embraced by the present invention and are readily prepared by contacting the free base with the appropriate mineral or organic acid in either aqueous solution or in a suitable organic solvent. The solid salt may then be obtained by precipitation or by evaporation of the solvent. The pharmaceutically acceptable acid addition salts of this invention include, but are not limited to, the hydrochloride, hydrobromide, hydroiodide, sulfate, bisulfate, nitrate, phosphate, acetate, lactate, maleate, fumarate, oxalate, citrate, tartrate, succinate, gluconate, methanesulfonate, and the like.

The novel aminothiazoles of this invention and their pharmaceutically acceptable acid addition salts are useful as anti-inflammatory agents and as regulants of the immune response in warm-blooded animals. The combination of anti-inflammatory activity and immune regulant activity is particularly valuable in the treatment of conditions such as rheumatoid arthritis and other diseases associated with immune deficiency and accompanied by inflammation. Thus, the compounds of the present invention act to relieve the pain and swelling associated with such conditions while also regulating the immune response of the subject and thereby alleviating the underlying immune disorder by maintaining immune competence. Accordingly, the present invention also embraces a method of treating rheumatoid arthritis in a warm-blooded animal by administering to the subject an effective anti-arthritic amount of an aminothiazole of the present invention or a pharmaceutically acceptable acid addition salt thereof. In accord with this method, the compounds of the present invention may be administered to the subject in need of treatment by conventional routes, such as orally or parenterally, dosages in the range of about 0.10 to about 50 mg/kg body weight of the subject per day, preferably about 0.15 to about 15 mg/kg body weight per day being suitable. However, the optimum dosage for the individual subject being treated will be determined by the person responsible for treatment, generally smaller doses being administered initially and thereafter gradual increments made to determine the most suitable dosage. This will vary according to the particular compound employed and with the subject being treated.

The compounds may be used in pharmaceutical preparations containing the compound or a pharmaceutically acceptable acid addition salt thereof in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds may be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds may be combined with sterile aqueous or organic media to form injectable solutions or suspensions. For example, solutions of the aminothiazoles in sesame or peanut oil, aqueous propylene glycol and the like may be used, as well as aqueous solutions of water-soluble pharmaceutically acceptable acid addition salts of the compounds. The injectable solutions prepared in this manner may then be administered intravenously, interperitoneally, subcutaneously or intramuscularly, with intravenous and interperitoneal administration being preferred. For local treatment of inflammation the compounds may also be administered topically in the form of ointments, creams, pastes and the like in accord with conventional pharmaceutical practice.

The activity of the compounds of the present invention as anti-inflammatory agents may be determined by pharmacological tests, for example the standard carrageenin-induced rat foot edema test using the general procedure described by C. A. Winter et. al., see Proceedings of the Society of Experimental Biology in Medicine, Volume 111, page 544 (1962). In this test, anti-inflammatory activity is determined as the percent inhibition of edema formation in the hind paw of male albino rats (generally weighing about 150 to 190 grams) in response to a sub-plantar injection of carrageenin. The carrageenin is injected as a 1% aqueous suspension 1 hour after oral administration of the drug, which is normally given in the form of an aqueous solution or suspension. Edema formation is then assessed 3 hours after the carrageenin injection by comparing the initial volume of the injected paw and the volume after a 3 hour period. The increase in volume 3 hours after carrageenin injection constitutes the individual response.

Compounds are considered active if the response between the drug-treated animals (6 rats per group) and the control group, i.e. the animals receiving the vehicle alone, is found to be significant on comparison with the results afforded by standard compounds like acetylsalicyclic acid at 100 mg/kg or phenylbutazone at 33 mg/kg, both by the oral route of administration.

The immune regulant activity of the compounds of the present invention may be determined by such pharmacological tests as the stimulation in vitro of lymphocyte proliferation of murine thymus cells cultured in the presence of Concanavalin A (Con A), employing the general evaluation procedure of V. J. Merluzzi et. al., see Journal of Clinical and Experimental Immunology, Volume 22, page 486 (1975). In this study, four different levels of lymphocyte stimulation assay (LSA) activity were established for the compounds undergoing evaluation, viz., those equal to Con A alone; those superior to Con A activity but less than levamisole, the standard compound of choice in this area; those having an activity equal to levamisole; and those having an activity equal to levamisole; and those having an activity greater than levamisole. Compounds are considered to be active for the present purposes if they are superior to Concanavalin A.

The present invention is illustrated by the following examples. However, it should be understood that the invention is not limited to the specific details of these examples.

EXAMPLE 1

Phenethylamine (479 grams, 3.96 moles, Eastman Scintillation Grade) was dissolved in 3500 ml of diethyl ether and the solution was cooled to 0° C. Dry hydrogen chloride gas was bubbled through the stirred solution for 10 minutes and the resulting solids were filtered. The filtrate was then cooled and hydrogen chloride was bubbled through the solution for 10 minutes and the solids collected. This procedure was repeated until acidification of the filtrate with dry hydrogen chloride failed to yield any precipitate. The combined solids were dried in air and then over phosphorous pentoxide under vacuum to provide 514 grams (82%) of phenethylamine hydrochloride, m.p. 216°–218° C.

Phenethylamine hydrochloride (257 grams, 1.63 moles) and ammonium thiocyanate (123.6 grams, 1.63 moles) were heated to 160° C. in 340 ml bromobenzene under nitrogen. After heating for 90 minutes, the mixture was cooled to room temperature and then to 5° C. This procedure was repeated with a further batch of 257 grams of phenethylamine hydrochloride. The combined solids obtained in the above reaction were stirred in 1.5 l water and filtered. Recrystallization from isopropyl alcohol yielded 261.5 grams (45%) N-phenethylthiourea, m.p. 132°–134°.

EXAMPLE 2

N-phenethylthiourea (225 grams, 1.25 moles) and α-bromoacetophenone (250 grams, 1.25 moles, Aldrich Chem. Co.) in 1500 ml absolute ethanol were heated to reflux temperature for 2½ hours under nitrogen. After reducing the solvent volume by 10%, the reaction mixture was cooled to room temperature and then to 0° C. in an ice bath. The solids were filtered off, redissolved in 2,500 ml of absolute ethanol and heated to reflux. The solvent volume was reduced to 2000 ml and the reaction mixture cooled to 0° C. This procedure was repeated and after the second recrystallization the solids were collected and dried under vacuum over phosphorous pentoxide, yielding 365 grams (81%) of 2-phenethylamino-4-phenyl-thiazole hydrobromide, m.p. 169°–172° C.

Analysis: Calcd for $C_{17}H_{16}N_2S \cdot HBr$: C, 56.50; H, 4.74; N, 7.68. Found: C, 57.36; H, 5.04; N, 7.83.

EXAMPLE 3

N-phenethylthiourea (2.0 grams, 0.011 moles) and α-bromopropiophenone (2.34 grams, 0.011 moles, Aldrich Chem. Co.) in 10 ml absolute ethanol were heated to reflux temperature for 90 minutes under nitrogen. The ethanol was then removed under vacuum, excess ethyl acetate added and the solids filtered and dried over phosphorous pentoxide. Recrystallization from absolute ethanol yielded 2.86 grams (70%) of 2-phenethylamino-4-phenyl-5-methylthiazole hydrobromide, m.p. 172°–175° C.

Analysis: Calcd for $C_{18}H_{18}N_2S \cdot HBr$: C, 57.59; H, 5.10; N, 7.46. Found: C, 57.67; H, 5.11; N, 7.39.

EXAMPLE 4

Following the procedure of Examples 1 and 2, hydrohalide salts of the following compounds were prepared:

$$\underset{R_3}{\overset{R_2}{\diagdown}}\underset{S}{\diagdown}\overset{N}{\diagup}-NH-CH_2-CH_2-X$$

| Salt | X | R₂ | R₃ | m.p. °C. |
|---|---|---|---|---|
| HCl | phenyl | p-fluorophenyl | hydrogen | 163–165 |
| HBr | p-bromophenyl | phenyl | hydrogen | 171–174 |
| HBr | p-bromophenyl | phenyl | methyl | 150–151.5 |
| HBr | p-methoxyphenyl | phenyl | hydrogen | 169–171 |
| HBr | p-methoxyphenyl | phenyl | methyl | 149–150.5 |
| HCl | p-methoxyphenyl | p-fluorophenyl | hydrogen | 156–158 |

EXAMPLE 5

2-thenylamine (thienylmethylamine) (30 grams, 0.265 moles, Fairfield Chemical Co.) was dissolved in 400 ml of diethyl ether and cooled to 0° C. in an ice bath. Dry hydrogen chloride gas was bubbled through the solution for 5 minutes. The resulting solids were filtered and dried over phosphorous pentoxide to yield 26.7 grams (61%) of 2-thenylamine hydrochloride, m.p. 186°–190° C.

2-thenylamine hydrochloride (13.35 grams, 0.089 moles) and ammonium thiocyanate (7.4 grams, 0.089 moles) in 20 ml bromobenzene were heated to reflux temperature for 90 minutes. The reaction mixture was cooled and the filtered solids washed three times with water. Recrystallization from chloroform and drying over phosphorous pentoxide yielded 5.0 grams (33%) of N-thenylthiourea, m.p. 99°–101° C.

Analysis: Calcd for $C_6H_8N_2S_2$: C, 41.83; H, 4.68; N, 16.26. Found: C, 41.56; H, 4.58; N, 16.07.

EXAMPLE 6

N-thenylthiourea (2.0 grams, 0.0116 moles) and α-bromoacetophenone (2.3 grams, 0.0116 moles, Aldrich Chem. Co.) in 15 ml absolute ethanol were heated to reflux temperature for 90 minutes under nitrogen. The reaction mixture was cooled and the ethanol removed under vacuum. On dissolving the residue in hot isopropyl alcohol and diluting with diethyl ether, an oil was formed. The diethyl ether was decanted, the oil dissolved in a small amount of ethanol and cooled. The resulting solids were filtered and dried over phosphorus pentoxide, yielding 3.20 grams (78%) of 2-thenylamino-4-phenyl-thiazole hydrobromide, m.p. 115°–118° C.

Analysis: Calcd for $C_{14}H_{12}N_2S_2 \cdot HBr$: C, 47.58; H, 3.71; N, 7.93. Found: C, 47.75; H, 3.74; N, 7.90.

EXAMPLE 7

N-thenylthiourea (0.80 grams, 0.0046 moles) and α-chloro-p-fluoroacetophenone (0.80 grams, 0.0046 moles, Aldrich Chem. Co.) in 11 ml absolute ethanol were heated at reflux temperature under nitrogen for 90 minutes. After cooling, and ethanol was removed under vacuum and the solids triturated with ethanol, filtered and vacuum dried over phosphorous pentoxide, yielding 0.848 grams (56%) of 2-thenylamino-4(p-fluorophenyl)-thiazole hydrochloride, m.p. 184°–187° C.

Analysis: Calcd for $C_{14}H_{11}N_2S_2F \cdot HCl$: C, 51.45; H, 3.70; N, 8.57. Found: C, 51.41; H, 3.63; N, 8.39.

EXAMPLE 8

Following the procedures of Examples 6 and 7, hydrohalide salts of the following compounds were prepared:

| Salt | $R_2$ | $R_3$ | m.p. °C. |
|---|---|---|---|
| HBr | p-methoxyphenyl | hydrogen | 154–158 |
| HBr | phenyl | methyl | 179.5–181.5 |
| HCl | thienyl | hydrogen | 137–142 |

EXAMPLE 9

Furfurylamine (25.0 grams, 0.257 moles, Pfaltz & Bauer Co.) was dissolved in 1300 ml diethyl ether and cooled to 0° C. in an ice bath. Dry hydrogen chloride gas was bubbled through the solution until no further precipitation occurred. The solids were filtered and dried in vacuum over phosphorous pentoxide to yield 33.46 (97%) of furfurylamine hydrochloride, m.p. 147°–149° C.

Furfurylamine hydrochloride (33.46 grams, 0.250 moles) and ammonium thiocyanate (38.14 grams, 0.501 moles) in 71 ml bromobenzene were heated under nitrogen at reflux temperature for 20 minutes and then cooled to room temperature. The reaction mixture was mixed with a solution of 125 ml water and 100 ml ethyl acetate and left at room temperature overnight. The mixture was then diluted to give 500 ml ethyl acetate and 350 ml water and the aqueous layer separated. The organic layer was washed with water and dried over sodium sulfate. After filtration, the organic layer was evaporated to dryness and bromobenzene removed under vacuum. The resulting solids were ground in a mortar and pestle and the fine particles stirred in diethyl ether to remove residual bromobenzene. The solids were then filtered, washed with diethyl ether and vacuum dried over phosphorus pentoxide, yielding 12.06 grams (30%) of N-furfurylthiourea, m.p. 80°–91° C. Recrystallization from benzene gave yellow needles, m.p. 98°–100° C.

Analysis: Calcd for $C_6H_8N_2OS$: C, 46.14; H, 5.16; N, 17.93. Found: C, 46.42; H, 5.06; N, 17.88.

EXAMPLE 10

N-furfurylthiourea (0.82 grams, 0.005 moles) and α-bromopropiophenone (1.07 grams, 0.005 moles, Aldrich Chem. Co.) in 11 ml absolute ethanol were heated to reflux temperature under nitrogen for 3 hours. After cooling to room temperature, the solvent was removed under vacuum to give a thick brown oil, which was triturated with five 35 ml portions of refluxing ethyl acetate. The ethyl acetate was reduced in volume to about 25 ml and cooled to room temperature. The precipitated solids were filtered, washed with ethyl acetate and vacuum dried over phosphorous pentoxide, yielding 0.585 grams (33%) of 2-furfurylamino-5-methyl-4-phenyl-thiazole hydrobromide, m.p. 150°–153° C.

Analysis: Calcd for $C_{15}H_{14}N_2OS \cdot HBr$: C, 51.29; H, 4.30; N, 7.97. Found: C, 51.97; H, 4.47; N, 8.42.

EXAMPLE 11

Following the procedure of Examples 9 and 10, hydrohalide salts of the following compounds were prepared:

| Salt | $R_2$ | $R_3$ | m.p. °C. |
|---|---|---|---|
| HBr | phenyl | hydrogen | 123–126 |
| HBr | phenyl | phenyl | 192–194 |

EXAMPLE 12

The immune regulant activity of the aminothiazoles described in Examples 2, 3, 4, 6, 7, 8, 10 and 11 was evaluated by determining their ability to stimulate, in vitro the lymphocyte proliferation of murine thymus cells cultured in the presence of Concanavalin A (Con A) by employing the procedure of V. J. Merluzzi et. al., as essentially described in the *Journal of Clinical and Experimental Immunology*, Vol. 22, p. 486 (1975). The cells were derived from male C57B1/6 mice of from 6–8 weeks age, purchased from the Jackson Laboratories of Bar Harbor, Maine and the Con A was obtained from Sigma Chemicals of St. Louis, Mo. Each cell culture (consisting of 0.10 ml thymus cells stock solution, 0.05 ml of Con A stock solution and 0.05 ml of drug solution) was performed in quadruplicate and cellular proliferation was measured, after 48 hours of incubation at 37° C., by pulsing each culture with $^3$H-thymidine (0.01 ml of specific activity 1.9 C/mM, obtained from Schwarz-Mann, Inc. of Orangeburg, N.Y.) and then determining the incorporation of $^3$H-thymidine into cellular deoxyribonucleic acid (DNA) by an assessment of radioactivity using a liquid scintillation counter. The results obtained in this manner are expressed quantitatively in terms of the average counts per minute (cpm) or $^3$H-thymidine incorporated at the drug level with maximum activity by the quadruplicate cell cultures. These quadruplicate determinations are employed at eight different concentrations of drugs in the range 0.02 to 50 μg/ml. The highest cpm value obtained is employed in the scoring system. On this basis, four different levels of activity were established in the present lymphocyte stimulation assay (LSA) and these are defined in the manner hereinafter indicated, viz., those levels equal to Con A alone (6,000+300 cpm) were assigned a negative value or score of zero; those superior (10,000+700 cpm) to Con A activity but less than levamisole were scored as +; while those equal to levamisole (22,000±900 cpm) were scored as ++ and those having an activity (27,000±1,000 cpm) greater than levamisole were scored as +++. The LSA activity for the compounds described in the above Examples was +++ in each case.

EXAMPLE 13

The anti-inflammatory activity of aminothiazoles of this invention was determined using the standard carrageenin-induced rat foot edema test, according to the procedure essentially as described by C. A. Winter etl. al., and reported in the *Proceedings of the Society for Experimental Biology and Medicine*, Vol. 111, p. 544 (1962). The compounds were administered orally in the form of their previously reported hydrohalide salts at a dose level of 33 mg/kg. The results obtained in this manner are presented in the table below in terms of the percent inhibition of edema formation afforded by each test compound as compared to the non-drug treated control (i.e., aqueous solution with no compound):

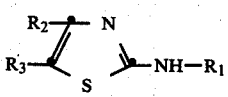

| $R_1$ | $R_2$ | $R_3$ | Salt | % Inhibition of edema (33 mg/kg, p.o.) |
|---|---|---|---|---|
| 2-thenyl | 4-fluorophenyl | hydrogen | HBr | 49 |
| 2-phenethyl | phenyl | hydrogen | HBr | 47 |
| 4-methoxyphenethyl | 4-fluorophenyl | hydrogen | HBr | 29 |

I claim:
1. A compound of the formula

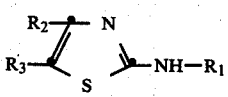

and the pharmaceutically acceptable acid solution salts thereof, wherein $R_1$ is selected from the group consisting of $-(CH_2)_2-X$, and $-(CH_2)_m Y$, wherein X is selected from the group consisting of phenyl and monosubstituted phenyl, said substituent being selected from the group consisting of alkyl of 1 to 3 carbon atoms, hydroxy, alkoxy of 1 to 3 carbon atoms, chloro, bromo and fluoro;

Y is selected from the group consisting of thienyl, monosubstituted thienyl, furyl and monosubstituted furyl, said substituent being selected from the group consisting of alkyl of 1 to 3 carbon atoms, chloro, bromo and fluoro;

m is an integer from 1 to 2;

$R_2$ is selected from the group consisting of phenyl, thienyl, and monosubstituted phenyl, said substituent being selected from the group consisting of alkyl of 1 to 3 carbon atoms, chloro, bromo and fluoro;

and $R_3$ is selected from the group consisting of hydrogen and alkyl of 1 to 3 carbon atoms.

2. A compound of claim 1 wherein $R_2$ is phenyl.
3. A compound of claim 2 wherein $R_3$ is hydrogen.
4. A compound of claim 1 wherein $R_1$ is $-(CH_2)_2-X$.
5. A compound of claim 4 wherein X is phenyl.
6. A compound of claim 5 wherein $R_2$ is phenyl.
7. A compound of claim 6 wherein $R_3$ is hydrogen.
8. A compound of claim 6 wherein $R_3$ is methyl.
9. A compound of claim 4 wherein X is p-methoxyphenyl, $R_2$ is p-fluorophenyl and $R_3$ is hydrogen.
10. A compound of claim 1 wherein $R_1$ is $-(CH_2)_m-Y$.
11. A compound of claim 10 wherein $R_2$ is phenyl or p-fluorophenyl.
12. A compound of claim 11 wherein $R_3$ is hydrogen or methyl.
13. A compound of claim 10 wherein Y is thienyl.
14. A compound of claim 13 wherein m is 1.
15. A compound of claim 14 wherein $R_2$ is phenyl.
16. A compound of claim 14 wherein $R_2$ is p-fluorophenyl.
17. A compound of claim 15 wherein $R_3$ is hydrogen.
18. A compound of claim 15 wherein $R_3$ is hydrogen.
19. A compound of claim 10 wherein Y is furyl.
20. A compound of claim 19 wherein m is 1 and $R_2$ is phenyl.
21. A compound of claim 20 wherein $R_3$ is hydrogen.
22. A compound of claim 20 wherein $R_3$ is methyl.
23. A pharmaceutical composition comprising an immune-regulant efective amount of a compound of claim 1 and a pharmaceutically acceptable carrier.
24. A composition of claim 23 wherein the compound is 2-phenylethylamino-4-phenyl-thiazole.
25. A composition of claim 23 wherein the compound is 2-thenylamino-4-(p-fluorophenyl)-thiazole.
26. A composition of claim 23 wherein the compound is 2-(p-methoxyphenethylamino)-4-(p-fluorophenyl)-thiazole.
27. A method of treating rheumatoid arthritis in a host which comprises administering to said host an effective anti-arthritic amount of a compound of claim 1.
28. A compound of claim 27 wherein the compound is 2-phenethylamino-4-phenyl-thiazole.
29. A method of claim 27 wherein the compound is 2-thenylamino-4-(p-fluorophenyl)-thiazole.
30. A method of claim 27 wherein the compound is 2-(p-methoxyphenethylamino)-4-(p-fluorophenyl)-thiazole.
31. A method of immune regulation in an animal which comprises administering to said animal an effective immune regulant amount of a compound of claim 1.
32. A method of claim 31 wherein the compound is 2-phenethylamino-4-phenyl-thiazole.
33. A method of claim 31 wherein the compound is 2-thenylamino-4-(p-fluorophenyl)-thiazole.
34. A method of claim 31 wherein the compound is 2-(p-methoxyphenethylamino)-4-(p-fluorophenyl)-thiazole.

* * * * *

UNITED STATES PATENT OFFICE
CERTIFICATE OF CORRECTION

Patent No. 4,307,106    Dated December 22, 1981

Inventor(s) Joseph G. Lombardino

It is certified that error appears in the above-identified patent and that said Letters Patent are hereby corrected as shown below:

Column 3, line 1, "bromobenene" should read --bromobenzene--

Column 9, line 47 (line 3 of claim 1), "solution" should read --addition--.

Signed and Sealed this

Sixteenth Day of March 1982

|SEAL|

*Attest:*

*Attesting Officer*

GERALD J. MOSSINGHOFF

*Commissioner of Patents and Trademarks*